United States Patent
Murray et al.

(10) Patent No.: US 7,798,000 B1
(45) Date of Patent: Sep. 21, 2010

(54) NON-DESTRUCTIVE IMAGING, CHARACTERIZATION OR MEASUREMENT OF THIN ITEMS USING LASER-GENERATED LAMB WAVES

(75) Inventors: Todd W. Murray, Roslindale, MA (US); Claire Prada, Paris (FR); Oluwaseyi Balogun, Livermore, CA (US)

(73) Assignee: Trustees of Boston University, Boston, MA (US)

( * ) Notice: Subject to any disclaimer, the term of this patent is extended or adjusted under 35 U.S.C. 154(b) by 992 days.

(21) Appl. No.: 11/588,823

(22) Filed: Oct. 27, 2006

Related U.S. Application Data

(60) Provisional application No. 60/731,437, filed on Oct. 28, 2005.

(51) Int. Cl.
*G01N 29/12* (2006.01)
(52) U.S. Cl. .............................. 73/597; 73/579; 73/596; 73/602
(58) Field of Classification Search .................. 73/597, 73/623, 638, 643, 644, 624, 626, 628, 629, 73/600, 602, 579, 596
See application file for complete search history.

(56) References Cited

U.S. PATENT DOCUMENTS 5,767,410 A * 6/1998 Lareau et al. ................. 73/623
6,595,061 B2 * 7/2003 Gorman et al. ............... 73/597
6,766,693 B1 * 7/2004 Light et al. ................... 73/622
6,799,466 B2 * 10/2004 Chinn .......................... 73/622
6,996,480 B2 * 2/2006 Giurgiutiu et al. ............ 702/35
7,647,829 B2 * 1/2010 Junker et al. ................. 73/592

OTHER PUBLICATIONS

Murray, T. et al., "High-Frequency Laser Based Acoustic Microscopy Using a CW Generation Source," Proceedings of 16th World Conference on Non-Destructive Testing, 2004, Montreal, Canada. Retrieved from http://www.ndt.net/article/wcndt2004/pdf/laser_ultrasonics/571_murray.pdf.

* cited by examiner

*Primary Examiner*—J M Saint Surin

(57) ABSTRACT

A laser-based ultrasonic technique for the inspection of thin plates and membranes employs an amplitude-modulated laser source to excite narrow bandwidth Lamb waves. The dominant feature in the acoustic spectrum is a sharp resonance peak that occurs at the minimum frequency of the first-order symmetric Lamb mode, where the group velocity of the Lamb wave goes to zero while the phase velocity remains finite. Experimental results with the laser source and receiver on epicenter demonstrate that the zero group velocity resonance generated with a low power modulated excitation source can be detected using an optical probe such as a Michelson interferometer coupled to a lock-in amplifier. This resonance peak is sensitive to the thickness and mechanical properties of plates and may be suitable, for example, for the measurement and mapping of nanoscale thickness variations.

19 Claims, 4 Drawing Sheets

NON-DESTRUCTIVE IMAGING, CHARACTERIZATION OR MEASUREMENT OF THIN ITEMS USING LASER-GENERATED LAMB WAVES

CROSS REFERENCE TO RELATED APPLICATIONS

This Patent Application claims the benefit under 35 U.S.C. §119(e) of U.S. Provisional Patent Application No. 60/731,437 filed Oct. 28, 2005 entitled Laser Generation Of Quasi-Resonance Modes In Single And Multi-Layered Plates, Coatings And Films For High Resolution Imaging, Materials Characterization And Thickness Measurements, the contents and teachings of which are hereby incorporated by reference in their entirety.

STATEMENT OF GOVERNMENT RIGHTS

The invention was made with Government support under contract numbers ECS0210752 and ECS030446 awarded by the National Science Foundation. The Government has certain rights in the invention.

BACKGROUND

It is known to perform quantitative, non-destructive evaluation of thin items such as plates and membranes though the analysis of guided Lamb wave propagation in these structures. Laser-based ultrasonic inspection of thin plates has been studied both theoretically and experimentally. A pulsed laser source can be used to generate broadband Lamb waves that are detected, after some propagation distance, with an optical probe, and phase velocity dispersion characteristics are subsequently used to determine physical or mechanical properties of the plate. Narrow bandwidth techniques have also been used to generate Lamb waves at a single phase velocity or at a single wavelength.

Lamb waves exhibit interesting behavior at specific frequencies where the group velocity vanishes while the phase velocity remains finite. This phenomenon is observed in homogeneous, isotropic materials at the minimum frequency of the first symmetric ($S_1$) mode, and can also be observed for higher modes. The $S_1$ mode phase velocity appears to be double-valued over a small frequency range above a minimum frequency. The upper portion of the $S_1$ curve, above a "zero group velocity" point ZGV, is classified as part of the $S_2$ mode which may be viewed as a "backwards wave" $S_{2b}$ having phase velocity and group velocity of opposite sign. The $S_1$ mode, on the other hand, starts at the ZGV point and continues out to higher frequencies. Just above the minimum frequency, the $S_1$ and $S_{2b}$ modes interfere, having very close phase velocities and near zero group velocities. Due to the fact that both modes have zero group velocity at the ZGV point, energy coupled into the plate is not transmitted away from the excitation point and a resonance, sometimes referred to as a thickness quasi-resonance, occurs. The frequency of this resonance is slightly lower (roughly 2% to 10%) than the well-known longitudinal or shear thickness resonance associated with the $S_{2b}$ cut-off frequency.

It has been suggested that the zero group velocity resonance be utilized for materials characterization applications. Experimenters have observed strong transmission through a plate using air coupled ultrasound transducers at the minimum frequency of the $S_1$ mode, and have used this resonance to measure thickness variations in millimeter-scale plates.

SUMMARY

An amplitude-modulated laser source is utilized to excite a predetermined Lamb wave in an item such as a thin plate, such that a high quality factor (high-Q) resonance peak with a large out of plane displacement component occurs. The resonance peak corresponds to the ZGV point of the Lamb wave, which may be for example the $S_1$ wave or a higher-order wave, and it can be detected using an optical probe such as an optical interferometer. The center frequency of the resonance peak is sensitive to the local thickness and mechanical properties of the item, and this sensitivity may be exploited to measure nanometer-scale thickness variations in plates. Additionally, the Q of the resonance peak is sensitive to the local acoustic attenuation of the item, and this sensitivity may be exploited to measure material density and/or other characteristics that contribute to acoustic attenuation. The disclosed technique has advantages over an air-coupled approach in that its frequency range is not limited by sound attenuation in the air, and is thus suitable for the inspection of micron scale thin plates and membranes, More specifically, a disclosed method includes directing a source laser beam to a test location on a thin item, the source laser beam being amplitude modulated in a manner effective to excite a predetermined Lamb wave at a detection location of the item, the predetermined Lamb wave having zero group velocity and a finite phase velocity. In one embodiment, the source laser may be a continuous-wave (CW) laser with substantially sinusoidal amplitude modulation. In another embodiment, a pulse mode of laser operation may be utilized in which the pulse duration is sufficiently short such that the modulation spans a frequency range of interest.

The vibration of the item is sensed at the detection location in a frequency range in which a resonance peak corresponding to the predetermined Lamb wave is expected to be found. The resonance peak is detected and a value of a predetermined characteristic of the resonance peak is calculated. Examples of such characteristics include the frequency of the resonance peak as well as its quality factor or "Q". The frequency is related to the local thickness of the item, and thus minute variations of the resonance frequency can be used to measure corresponding minute variations in the item thickness. The Q can be influenced by the local attenuation characteristics of the item, which may be determined in part by material density, molecular structure, presence of voids or other defects, etc.

In one embodiment, the predetermined Lamb wave is a symmetric, first-order ($S_1$) Lamb wave which has a relatively high-amplitude resonance peak. Other Lamb waves may be utilized either instead of or in addition to the $S_1$ wave.

In one embodiment, the vibration of the item is sensed utilizing an optical probe coupled to the detection location. Examples of suitable optical probes include laser interferometers, piezo-optic probes, and so-called "knife edge" probes.

While the disclosure is directed primarily to testing/measuring of items such as thin plates etc., the disclosed technique can also be utilized in other applications such as sensing applications in which a surface of a substrate is "functionalized" to selectively retain a substance such as a chemical or biological agent whose presence is to be detected. The laser-based detection technique can be used to excite a Lamb resonance in the substrate having a characteristic whose value is sensitive to the presence or absence of the substance on the functionalized surface. This characteristic may be frequency, Q, or some combination of the two characteristics for example.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Figure 1:
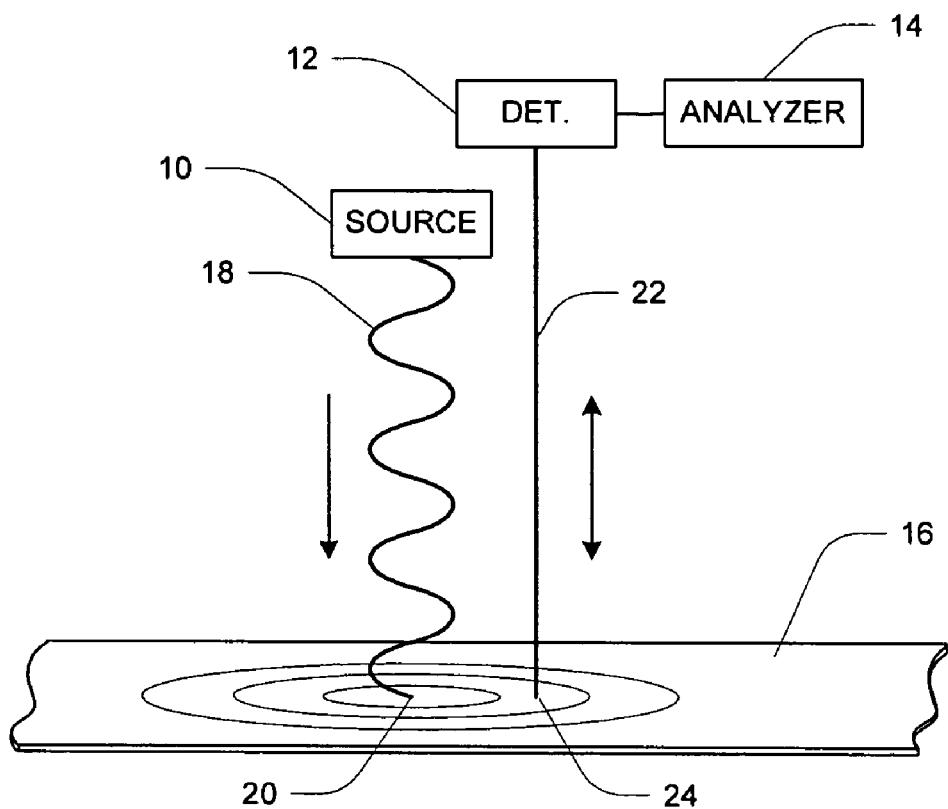
FIG. 1 is a simplified schematic diagram of a system for non-destructive measurement of a thin item in accordance with the present invention.

FIG. 1 shows a measurement system including source laser apparatus (SRC) 10, a detector (DET) 12, and an analyzer 14 for performing measurements on a thin item 16. The source laser apparatus 10 generates a source laser beam 18 and directs it to a test location 20 of the item 16. As indicated by its wavy depiction, the source laser beam 18 includes amplitude modulation which may be in form, for example, of a substantially sinusoidal modulation of continuous-wave (CW) source laser. The detector 12 may include an optical probe that generates a detection laser beam 22 impinging on the item 16 at a detection location 24 and reflected back to an optical detection component within the detector 12. The output of such detection component is provided to an analyzer 14 utilized to detect certain characteristics of the signal generated by the detector 12. Specific examples of the source laser apparatus 10, detector 12 and analyzer 14 as well as specific mode of their operation are described below.

Generally, the purpose of the amplitude-modulated source laser beam 18 is to excite a predetermined Lamb wave in the item 16 and, based on characteristics of the Lamb wave, determine the value of a corresponding characteristic of the item 16 to which the Lamb wave is sensitive. As an example, the frequency of a Lamb wave in an item is particularly sensitive to the thickness of the item. It can also be shown that the quality factor (Q) of certain Lamb resonances is sensitive to attenuation characteristics of the item. The Lamb wave is detected by the detector 12, and the frequency and/or quality factor (Q) or other characteristics of the Lamb wave are provided to the analyzer 14, which converts the value(s) of such characteristic(s) into a corresponding value (such as thickness) for the item 16.

Figure 2:
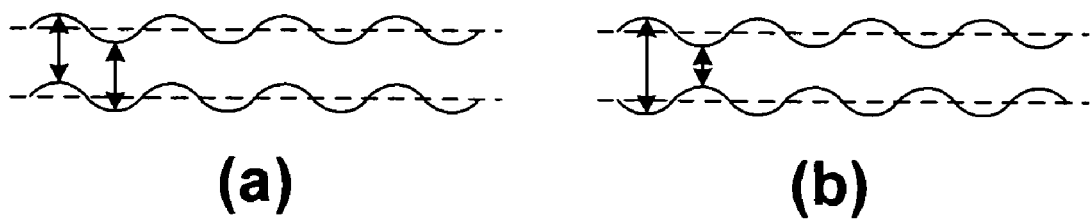
FIG. 2 (consisting of FIGS. 2(a) and 2(b)) is diagram illustrating the structure of Lamb waves in a thin item.

FIG. 2 illustrates Lamb waves. Lamb waves are a form of so-called "plate" waves that propagate across thin items such as plates, films, membranes, etc. FIG. 2(a) illustrates "asymmetric" Lamb waves, in which the wave disturbance is a shear disturbance in the direction orthogonal to the surface of the item. As shown, both of the surfaces of the item experience displacement in the same direction. FIG. 2(b) shows "symmetric" Lamb waves, in which the disturbance is in the form of compression and rarefaction in the direction orthogonal to the surface. In addition to symmetry/asymmetry, Lamb waves are also characterized by their "order", which corresponds to their wave number or spatial frequency.

Figure 3:
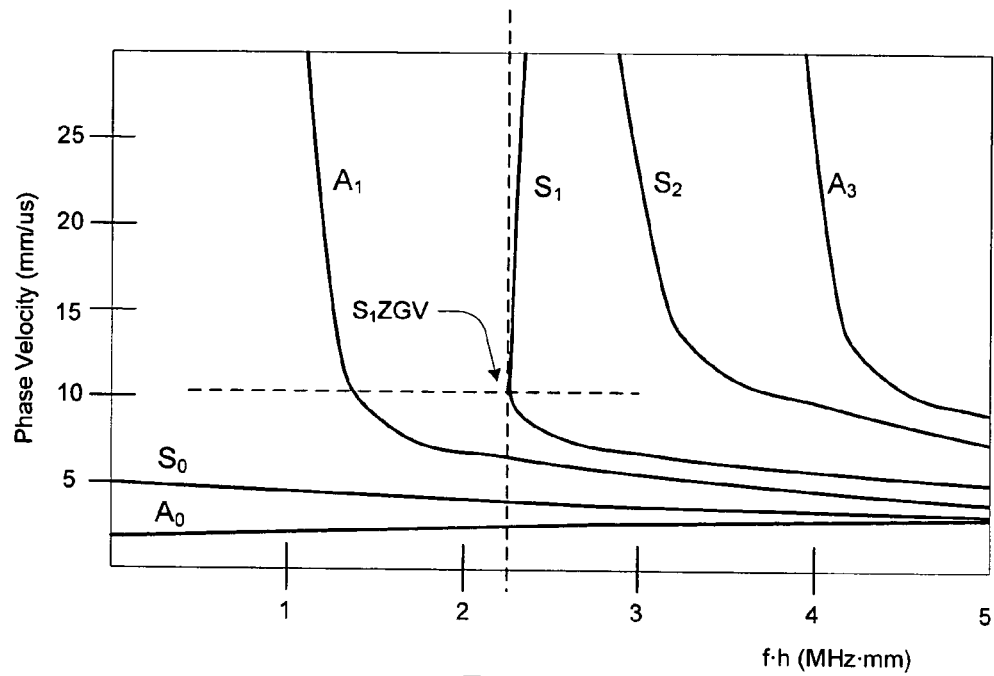
FIG. 3 is a dispersion plot of phase velocity versus the product of frequency (f) and thickness (h) for various Lamb waves in a thin item.

Lamb waves exhibit interesting behavior at specific frequencies where their group velocity vanishes while their phase velocity remains finite. This phenomenon is observed in homogeneous, isotropic materials at the minimum frequency of the first symmetric ($S_1$) mode, and can also be observed for higher modes. FIG. 3 shows a phase velocity dispersion curve over a limited frequency range in a material with Poisson ratio of 0.355. The $S_1$ mode appears to be double valued over a small frequency range above a frequency corresponding to a point identified as "$S_1$ZGV" (which stands for "$S_1$ zero group velocity"). In some analyses, the upper portion of this curve (extending upward from $S_1$ZGV) is classified as a "backwards wave" of the $S_2$ mode and may be labeled as $S_{2b}$, where "backwards" indicates that the phase velocity and group velocity of this mode are of opposite sign. In the neighborhood of $S_1$ZGV, the $S_1$ and $S_{2b}$ modes interfere with each other, having very close phase velocities and near zero group velocities. Because both modes have zero group velocity at the ZGV point, energy coupled into the item is not transmitted away from the excitation point, and a resonance (sometimes referred to as a "thickness quasi-resonance") occurs. The frequency of this resonance is slightly lower (roughly 2% to 10%) than the well-known longitudinal or shear thickness resonance associated with the $S_{2b}$ cut-off frequency.

Figure 4:
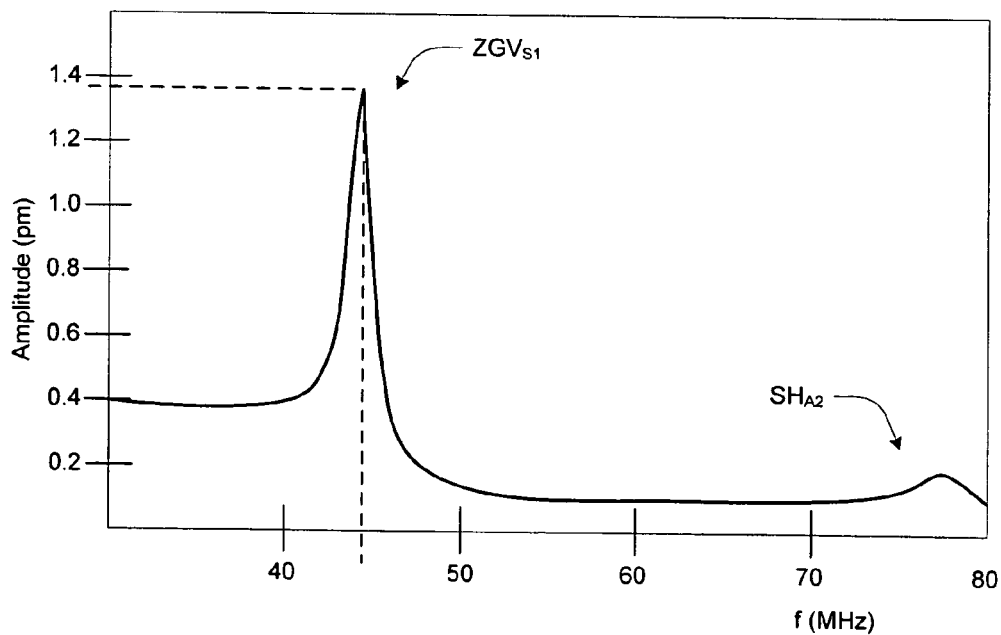
FIG. 4 is a spectrum plot of amplitude versus frequency for detected vibration of a thin item.

FIG. 4 illustrates this $S_1$ resonance for a representative item 16, which in this case is a 50-micron thick tungsten plate. Specifically, the $S_1$ resonance appears as a strong peak of acoustic energy at about 45 MHz. A second, much smaller, peak appears at about 77 MHz and is associated with the shear-type $A_2$ mode ($SH_{A2}$). For an arbitrary item, it may be necessary to perform some amount of analysis and characterization to identify the frequency and amplitude that are expected for the $S_1$ or other resonance that is to be employed in measuring or imaging the item. Examples of such analysis are presented below. Once such characterization has been performed, a measuring/imaging system can be configured in an appropriate manner to selectively identify the resonance of interest, to the exclusion of other, non-pertinent resonances that may be present. For imaging a 50-micron tungsten plate, for example, a measuring/imaging system would be configured to identify and analyze a resonance peak in the vicinity of 45 MHz, within some relatively narrow range determined by expected variations over a population of such items, and to ignore acoustic energy in the area of 77 MHz for example.

As noted above, the phenomenon of zero group velocity resonance has been suggested for materials characterization applications (including imaging thickness variations in millimeter-scale plates) using air coupled ultrasound transducers at the minimum frequency of the $S_1$ mode. The presently disclosed technique is directed to using thermoelastic laser excitation, which has been found to couple very efficiently into the ZGV resonance leading to a large out-of-plane displacement that can be measured using an optical interferometer. This has some advantages over the air-coupled approach in that it is not limited in frequency range by sound attenuation in the air, and is thus suitable for the inspection of even thinner items such as micron-scale plates, films and membranes.

Figure 5:
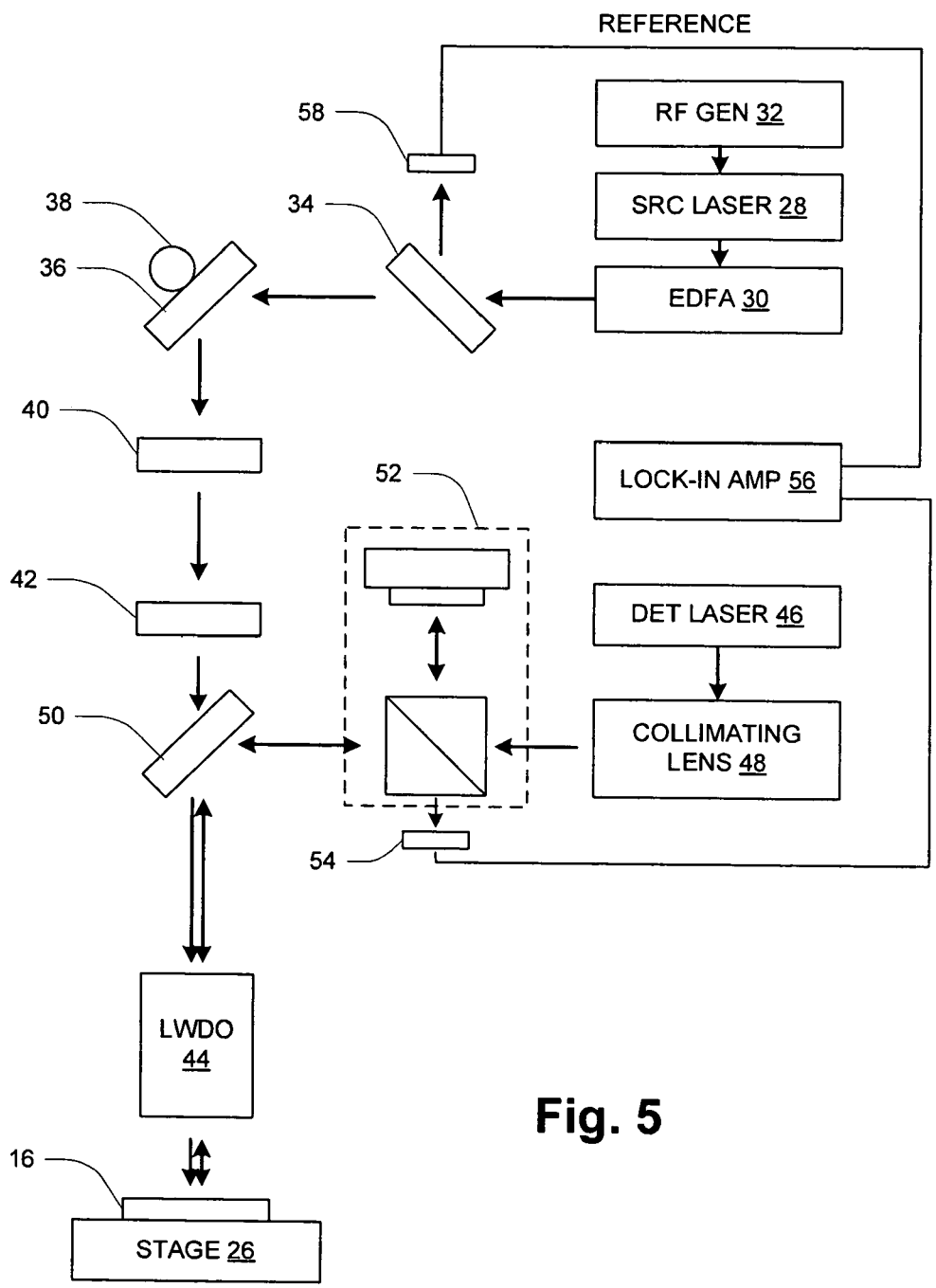
FIG. 5 is a block diagram of a laser-based acoustic microscope which can be utilized in an embodiment of the non-destructive measurement system of FIG. 1.

FIG. 5 illustrates an apparatus that may be employed in performing measurement and/or imaging in accordance with the disclosed technique. A laser-based ultrasonic microscopy system has two paths that lead to a surface of an item 16 which is mounted on a stage 26. In the first path, a source laser 28 is a 1550 nm electro-absorption modulated distributed-feedback (DFB) diode laser and is followed by a 1 W erbium-doped fiber amplifier (EDFA) 30. The source laser 28 is amplitude modulated by a radio-frequency (RF) signal generator 32 capable of producing signals in a frequency range of interest. The light from the EDFA 30 is directed through a beam splitter 34 to a mirror 36 on a gimbal mount 38, from which it travels though a relay lens system including lenses 40 and 42 and through a long-working-distance objective (LWDO) 44 to the item 16. In the illustrated embodiment, a maximum of 500 mW of average source power makes it through the lens system to the item 16. The gimbal mount 38 of the mirror 36 is used to control the generation point within the field of view of the microscope.

In the second path, detection laser light is generated by a detection laser 46, is collimated by collimating lens 48, and directed to the item via mirror 50 and LWDO 44. The light reflected from the item is sent to a stabilized Michelson interferometer 52 where the acoustic signal of interest is detected. The detection laser 46 is a 200 mW frequency doubled Nd:YAG laser, and it is attenuated such that approximately 3 mW of optical power is incident on a photodiode detector 54. The output signal from the detector 54 is sent to an RF lock-in amplifier 56 where the magnitude and phase of the detected acoustic signal are recorded. Note that the mirror 34 and a second photodiode detector 58 are used to sample a small fraction of the source beam to serve as a reference to the lock-in amplifier 56.

In one set of experiments conducted using the apparatus of FIG. 5, the phase velocity dispersion characteristics of a plate in the vicinity of the ZGV point were measured. The excitation and detection laser spot sizes were approximately 5 um and 0.6 um, respectively. Measurements were taken across a set of separation distances between the test location 20 and the detection location 24 extending from 10 um to 600 um in steps of 10 um. At each separation, the real and imaginary components of the acoustic field were recorded in the temporal frequency range of 40 to 48 MHz in steps of 0.1 MHz. At each temporal frequency, the data taken over all spatial steps was collected and a spatial Fourier transform was applied. The spatial frequencies of the laser generated acoustic modes were then determined by identifying the peaks in the power spectrum, and the dispersion curve was constructed by dividing the excitation frequency by the measured spatial frequency of each mode to yield the phase velocity. These experiments are in the nature of the pre-characterization of an item to be tested/measured, as discussed above.

Results similar to those shown in FIG. 3 were obtained. Note that the phase velocity of the $S_{2b}$ mode was found to be negative, and thus the plot in FIG. 3 for this mode is of the magnitude of the phase velocity. A simplex optimization routine was used to determine the best fit plate thickness, using only the first two Lamb wave modes ($A_0$ and $S_0$), and this gave a plate thickness of 50.8 um, which is in good agreement with the manufacturer's specification of 50 um. A total of five modes were detected over this frequency range. The first three modes show excellent agreement with theory, while the $S_1$ and $S_{2b}$ modes are shifted by approximately 7%. The reason for this shift is unclear, but similar results (2%-10% discrepancy) were obtained on other samples, and it is postulated that the shift may be due to processing-induced anisotropy. It is also interesting to point out that the $S_1$ and $S_{2b}$ modes do not fully converge at the ZGV point in the experimental measurement, but rather follow a more horizontal path towards the lower frequencies. A purely complex mode exists in this region, and it is believed that this feature in the experimental data can be attributed to the detection of this non-propagating mode.

In order to evaluate the zero group velocity resonance, the source beam and detector beam were aligned on epicenter at the surface of the item 16 and the spot size of the source beam was expanded to 25 um by adjusting the position of the relay lens 40, 42 to slightly defocus this beam on the item surface. The reason for defocusing the source beam was to reduce background thermal effects. The modulation frequency was then scanned between 38 MHz and 80 MHz in steps of 0.1 MHz, and at each frequency the magnitude of the acoustic signal was recorded.

Results like those shown in FIG. 4 were obtained. The prominent feature in the spectrum is a sharp resonance occurring at approximately 44.6 MHz. Referring back to FIG. 3, it can be seen that this resonance occurs very near the zero group velocity point in the dispersion curve, and is clearly not associated with a conventional longitudinal or shear thickness resonance. The only other feature in the spectrum of FIG. 4 is a small, somewhat broader peak observed at about 77.8 MHz, which as discussed above is the thickness mode shear resonance that occurs at the cut-off frequency of the $A_2$ mode. For a plate thickness of 50 um and a transverse wave speed of 2.64 mm/s, this resonance is expected to occur at 77.9 MHz, which is in good agreement with the measured value.

It should be noted that results similar to those described above have been obtained on a 100-um tungsten plate and on aluminum plates of varying thicknesses. On these materials, the resonance appears to be localized and is insensitive to the distance between the test location 20 and the boundaries of the item 16. Measurements on nickel and zinc plates of similar thickness showed some distortion in the ZGV resonance peak that can most likely be attributed to grain boundary scattering.

It should also be noted that a pulse type of amplitude modulation may be employed in lieu of the frequency-scanned approach discussed above. If the pulse duration is sufficiently short, then acoustic energy across an entire frequency range of interest can be generated. Resonance peak(s) within the frequency range can be detected and analyzed to extract the desired information.

One potential application of the ZGV resonance is precision mapping of thickness variations in thin plates. FIG. 4 indicates that there may be sufficient sensitivity to measure frequency shifts in the resonance peak of less than 0.1 MHz. A frequency shift $\Delta f$ corresponds to a thickness variation $\Delta h = (h \cdot \Delta f)/f$. In the specific example of FIG. 5, for a ZGV resonance frequency of 44.6 MHz and a plate thickness of 50.8 um, thickness variations as small as 114 nm (approximately 0.2%) can be observed. Generally, some damping mechanism of the item 16 is responsible for limiting the quality factor and thus the achievable resolution. Damping and other effects may be influenced, for example, by surface roughness, material attenuation, and nonparallel plate boundaries. The results of FIG. 4 are from one measurement of one type of item. In alternative embodiments, the Q and thickness resolution may be substantially sharper or broader depending on the characteristics of the item.

Figure 6:
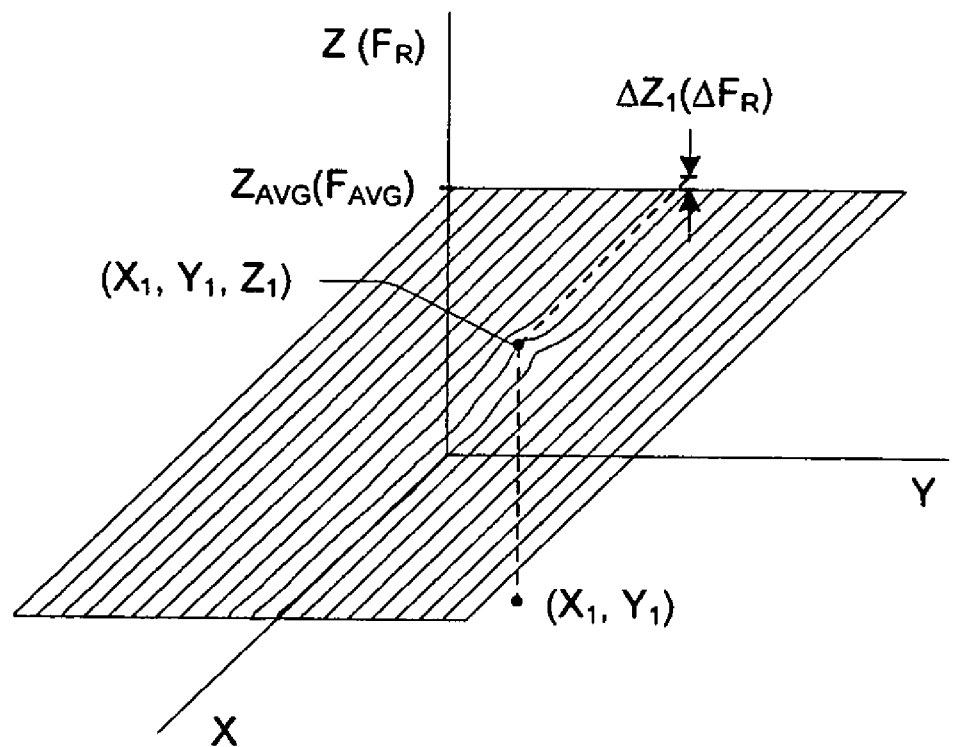
FIG. 6 is a three-dimensional plot illustrating an array of measurements taken over a two-dimensional extent of an item.

FIG. 6 illustrates in simplified form how a 2-dimensional image of thickness or other characteristic across an item can be generated. In the simplified representation, the item is a rectangular flat sheet having two adjacent edges that are taken to define X and Y axes. The Z axis in the plot is the measured value of the characteristic of interest (such as resonant frequency $F_R$) of the detected Lamb mode resonance. In the simplified example, it is assumed that the measured value Z is a substantially constant value $Z_{AVG}$ everywhere except in the vicinity of a point (X1, Y1), where the measured value Z1 is greater than $Z_{AVG}$. The difference $\Delta Z_1$ corresponds to a shift of the resonance frequency by an amount $\Delta F_R$ from an average resonance frequency $F_{AVG}$ seen across the entire plate. The value $\Delta F_R$ in turn can be converted into a deviation of the thickness of the item from an average thickness, for example.

While the above disclosure is directed primarily to testing/measuring of items such as thin plates etc., the disclosed technique can also be utilized in other applications. Such applications include sensors in which a surface of a sensor substrate is "functionalized" to selectively retain a substance such as a chemical or biological agent whose presence in the environment is to be detected. The laser-based detection technique can be used to excite a Lamb resonance in the substrate having a characteristic whose value is sensitive to the presence or absence of the substance on the functionalized surface. This characteristic may be frequency, Q, or some combination of the two characteristics for example.

While various embodiments of the invention have been particularly shown and described, it will be understood by those skilled in the art that various changes in form and details may be made therein without departing from the spirit and scope of the invention as defined by the appended claims.

What is claimed is:

1. A method, comprising:
    directing a source laser beam to a test location on a thin item, the source laser beam being amplitude modulated in a manner effective to excite a predetermined Lamb wave at a detection location of the item, the predetermined Lamb wave having zero group velocity and a finite phase velocity;
    sensing vibration of the item at the detection location in a frequency range in which a resonance peak corresponding to the predetermined Lamb wave is expected to be found; and
    detecting the resonance peak and calculating a value of a predetermined characteristic of the resonance peak,
    wherein the predetermined characteristic is selected from the group consisting of a center frequency of the resonance peak and a quality factor (Q) of the resonance peak, and further comprising (1) in the case that the predetermined characteristic is the center frequency of the resonance peak, converting the center frequency of the resonance peak to a corresponding thickness value representing the thickness of the item at the test location, and (2) in the case that the predetermined characteristic is the quality factor of the resonance peak, converting the quality factor of the resonance peak to a corresponding attenuation value representing the attenuation of the item at the test location.

2. A method according to claim 1, wherein the predetermined Lamb wave is a symmetric, first-order ($S_1$) Lamb wave.

3. A method according to claim 1, wherein the detection location is co-incident with the test location.

4. A method according to claim 1, wherein the test location is on a first surface of the item and the detection location is on a second surface of the thin item directly opposite the test location.

5. A method according to claim 1, wherein sensing the vibration of the item comprises utilizing an optical probe coupled to the detection location.

6. A method according to claim 5, wherein the detection location is co-incident with the test location.

7. A method according to claim 1, wherein the source laser beam is a continuous-wave laser beam modulated by a substantially sinusoidal modulating signal swept across the frequency range in which the resonance peak is expected to be found.

8. A method according to claim 1, wherein the source laser beam is a pulsed laser beam having pulse width sufficiently short to generate substantial energy across the frequency range in which the resonance peak is expected to be found.

9. A method according to claim 1, wherein the thin item has a non-planar curved shape.

10. A method according to claim 1, wherein the test location comprises a functionalized surface of the item operative to selectively retain a substance whose presence is to be detected, and wherein the predetermined characteristic of the resonance peak is a characteristic whose value is sensitive to the presence or absence of the substance on the functionalized surface.

11. Apparatus, comprising:
    source laser apparatus operative to direct a source laser beam to a test location on a thin item, the source laser beam being amplitude modulated in a manner effective to excite a predetermined Lamb wave at a detection location of the item, the predetermined Lamb wave having zero group velocity and a finite phase velocity;
    a detector operative to detect vibration of the item at the detection location in a frequency range in which a resonance peak corresponding to the predetermined Lamb wave is expected to be found; and
    an analyzer operative to detect the resonance peak and calculate a value of a predetermined characteristic of the resonance peak,
    wherein the predetermined characteristic is selected from the group consisting of a center frequency of the resonance peak and a quality factor (Q) of the resonance peak, and further comprising (1) in the case that the predetermined characteristic is the center frequency of the resonance peak, converting the center frequency of the resonance peak to a corresponding thickness value representing the thickness of the item at the test location, and (2) in the case that the predetermined characteristic is the quality factor of the resonance peak, converting the quality factor of the resonance peak to a corresponding attenuation value representing the attenuation of the item at the test location.

12. Apparatus according to claim 11, wherein the predetermined Lamb wave is a symmetric, first-order ($S_1$) Lamb wave.

13. Apparatus according to claim 11, wherein the analyzer includes an optical probe coupled to the detection location to detect the vibration of the item.

14. Apparatus according to claim 13, wherein the optical probe comprises an optical interferometer.

15. Apparatus according to claim 13, wherein the optical probe comprises a piezo-optic detector.

16. Apparatus according to claim 13, wherein the optical probe comprises a knife-edge detector.

17. Apparatus according to claim 11, wherein the detection location is co-incident with the test location.

18. Apparatus according to claim 11, wherein the source laser beam is a continuous-wave laser beam modulated by a substantially sinusoidal modulating signal swept across the frequency range in which the resonance peak is expected to be found.

19. Apparatus according to claim 11, wherein the source laser beam is a pulsed laser beam having pulse width sufficiently short to generate substantial energy across the frequency range in which the resonance peak is expected to be found.

* * * * *

UNITED STATES PATENT AND TRADEMARK OFFICE
CERTIFICATE OF CORRECTION

PATENT NO. : 7,798,000 B1
APPLICATION NO. : 11/588823
DATED : September 21, 2010
INVENTOR(S) : Todd W. Murray, Claire Prada and Oluwaseyi Balogun It is certified that error appears in the above-identified patent and that said Letters Patent is hereby corrected as shown below:

Title Page, Item (73) "Assignee" should read --Trustees of Boston University, Boston, MA (US) and Centre National de la Recherche Scientifique, Paris, FRANCE--.

Title Page, Item (74) "Attorney, Agent or Firm" should read --BainwoodHuang--.

Signed and Sealed this

Twenty-third Day of November, 2010

David J. Kappos
*Director of the United States Patent and Trademark Office*